(12) United States Patent
Kim

(10) Patent No.: US 8,691,283 B2
(45) Date of Patent: *Apr. 8, 2014

(54) STANDARDIZED BEE VENOM PREPARATION

(71) Applicant: Christopher M. Kim, Seoul (KR)

(72) Inventor: Christopher M. Kim, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/849,878

(22) Filed: Mar. 25, 2013

(65) Prior Publication Data

US 2013/0216517 A1  Aug. 22, 2013

Related U.S. Application Data

(60) Continuation of application No. 12/152,216, filed on May 13, 2008, now Pat. No. 8,440,234, which is a continuation of application No. 10/690,772, filed on Oct. 22, 2003, now abandoned, which is a division of application No. 09/615,437, filed on Jul. 13, 2000, now abandoned.

(60) Provisional application No. 60/197,261, filed on Apr. 14, 2000.

(51) Int. Cl.
*A61K 31/00* (2006.01)
*A61K 38/46* (2006.01)
*A61K 38/47* (2006.01)
*A61P 23/02* (2006.01)
*A61P 19/02* (2006.01)

(52) U.S. Cl.
USPC ............. 424/539; 424/184.1; 424/94.62; 514/16.6; 514/16.8; 514/18.7

(58) Field of Classification Search
None
See application file for complete search history.

(56) References Cited

U.S. PATENT DOCUMENTS

| 3,163,871 | A |   | 1/1965  | Palmer          |         |
|-----------|---|---|---------|-----------------|---------|
| 4,716,120 | A |   | 12/1987 | Tsay et al.     |         |
| 4,739,531 | A |   | 4/1988  | Robson          |         |
| 4,963,356 | A |   | 10/1990 | Calenoff et al. |         |
| 5,226,901 | A |   | 7/1993  | Dhaliwal et al. |         |
| 5,958,887 | A |   | 9/1999  | Hansen et al.   |         |
| 6,029,863 | A |   | 2/2000  | Ogram           |         |
| 8,440,234 | B2| * | 5/2013  | Kim ............................ | 424/539 |

OTHER PUBLICATIONS

Banks et al. Chemistry and Pharmacology of Honey-bee Venom In: Piek T., ed. Venoms of the Hyemoptera, London: Academmic Press, 1986, pp. 329-416.
Benton et al., "Venom Collection from Honey Bees", Science, vol. 142, pp. 228-230, Oct. 1963.
Cerrato et al., A Therapeutic Bee Sting? Alternatives Complementary Therapies, pp. 57-58, Aug. 1998.
Kim et al., Rhumatologic 41(3): 233-236, 1989.
Kim, C.M.-H., "Apitherapy Bee Venom Therapy," Potentiating Health and the Crisis of the Immune System, Mizrahi et al., ed. Plenum Press, New York, 1997, pp. 243-269.
Koyama et al., Pain 84(2-3); 133-9, Feb. 2000.
Los Angeles County Department of Health Services Pharmaceutical Formulary Mar. 2000 edition, pp. 291-292.
Mueller et al., "Comparison of Vespid venoms collected by electrostimulation and by venom sac extraction", J Allergy and Clinical Immunology vol. 68 No. 4, pp. 254-261, Oct. 1981.
Simics, Mihaly. 'Bee Venom-Frequently Asked Questions.' American Bee Journal. 136:107-109, 1996.
Steigerwaldt F. Mathies and Damrau F. "Standardized Bee Venom (Sbv) Therapy of Arthritis," Industrial Medicine and Surgery 1966, 35: 1045-1050.

* cited by examiner

*Primary Examiner* — Phuong Huynh
(74) *Attorney, Agent, or Firm* — Lerner, David, Littenberg, Krumholz & Mentlik, LLP

(57) ABSTRACT

Bee venom may be administered in a standardized formulation with or without relatively small amounts of anesthetic. In particular, the results of the combination of venom and anesthetic dramatically decreased pain and discomfort for patients undergoing apitherapy.

11 Claims, No Drawings

STANDARDIZED BEE VENOM PREPARATION

The present application is a continuation of U.S. patent application Ser. No. 12/152,216, filed May 13, 2008, now U.S. Pat. No. 8,440,234, which is a continuation of U.S. patent application Ser. No. 10/690,772, filed Oct. 22, 2003, now abandoned, which is a divisional of U.S. patent application Ser. No. 09/615,437, filed Jul. 13, 2000, now abandoned, which claims the benefit of the filing date of U.S. Provisional Patent Application No. 60/197,261, filed Apr. 14, 2000, now expired, the disclosures of which are hereby incorporated by reference herein.

FIELD OF THE INVENTION

The present invention relates to the fields of medicine and pharmacy, and specifically to bee venom formulations and methods of making and using same.

BACKGROUND OF THE INVENTION

Apitherapy is the medicinal use of various products of *Apis mellifera* (the common honeybee) including raw honey, pollen, propolis, beeswax, royal jelly and venom. Various studies attribute antibacterial, antifungal, anti-inflammatory, antiproliferative and anticancer potentiating properties to honey.

In China, for example, raw honey is applied to burns as an antiseptic and a pain killer. Recently, propolis has been identified as containing substances called caffeic esters that inhibit the development of precancerous changes in the colon of rats given a known carcinogen. Preparations from pieces of honeycomb containing pollen are reported to be successful for treating allergies and bee pollen is touted as an excellent food. This review focuses on related research materials about bee venom to treat chronic inflammatory painful illness.

Indeed, various forms of apitherapy have been used since ancient times. Ancient writers as diverse as Hesiod (800 BC), Aristophanes (450-388 BC), Varro (166-27 BC) and Columella (First Century AD) all wrote on the cultivation of the hive. Hippocrates (460-377 BC), the Father of Medicine, used it and call it Arcanum—a very mysterious remedy. Galan (131-201 AD), the Father of Experimental Physiology, mentioned it in his treatises on medicine. Charlemagne (742-814 AD) is said to have had himself treated with bee stings. The Koran (XVI:71) refers to bee venom in the following terms: "There proceeded from their bellies a liquor wherein is a medicine for men." For apitherapy and the scientific understanding of bees, real progress began about 100 years ago when physician Phillip Terc of Austria advocated the deliberate use of bee stings in his work: Report about a Peculiar Connection Between the Beestings and Rheumatism.

Today's proponents of apitherapy cite the benefits of bee venom and other bee derived products for alleviating chronic pain and for treating many ailments including various rheumatic diseases involving inflammation and degeneration of connective tissue (e.g., several types of arthritis), neurological disease (migraine, peripheral neuritis, chronic low back pain), autoimmune disease (multiple sclerosis, lupus) and dermatological conditions (eczema, psoriasis, herpes virus infections). In contrast, interest in bees has been sporadic in conventional medicine, focusing mainly on two areas unrelated to the therapeutic uses proposed above. These areas are: (i) the danger of hypersensitivity reactions, including anaphylactic shock, from the sting of insects of the genus *Apis*; (ii) the use of bee venom itself as immunotherapy for allergic reaction to such stings, especially to prevent life-threatening anaphylactic reactions in adults.

Despite the promise of apitherapy in alternative medicine circles, for the reasons discussed above as well as the absence of standardized bee venom preparations and limited protocols for bee venom's effective use, the application of bee venom in mainstream medicine has languished. In addition to the foregoing, apitherapy is often painful. The use of actual bees for the administration of bee venom can be dangerous and difficult to control. It is also difficult for people to overcome their aversion to insects and being stung. Even if administered by less painful techniques, such as by acupuncture, bee venom itself causes a unique combination of pain, burning and irritation. Such therapy can leave one asking whether the treatment is worse than the condition. In view of the foregoing, there remains a need for standardized formulations and methods for administering apitherapy to patients in need of such therapies. Methods which avoid the use of actual bees and which can reduce the pain associated with apitherapy are particularly desirable. It is to these problems that the present invention is addressed.

SUMMARY OF THE INVENTION

In accordance with one aspect of the present invention, there is provided a standardized bee venom preparation suitable for administration by injection. This bee venom preparation comprises a liquid carrier which is mixed with between about 0.1 and about 10 milligrams (mg) by weight of bee venom per milliliter (mL) of liquid carrier. The preparation can also include excipients such as diluents, preservatives, buffers, viscosity modifiers, co-solvents and the like. Preferably, the bee venom will be provided in an amount of between about 0.5 and about 5.0 mg per mL of liquid carrier.

Preferably, the bee venom will also include between about 0.01 and about 1 mg of melittin and between about 80 to about 9500 micrograms (mcg) total protein per mL of carrier. Most preferably, the bee venom used will include between about 0.04 and about 0.05 mg of melittin and between about 800 to about 950 mcg total protein per mL of carrier.

Preferably, the standardized bee venom preparation in accordance with the present invention is filtered through a 25 micrometer (mcm) filter (or better) so as to remove bacteria, bacterial debris, viruses and other contaminants. The formulations of this aspect of the present invention are sufficiently pure to provide safe and effective therapy through a standard injection intradermally, subcutaneously or intramuscularly. They are more highly purified than other bee venom preparations known in the art. Yet they retain the most active components of bee venom and may be obtained using commercially viable technology. They therefore represent a unique compromise of safety and efficacy as well as convenience and cost.

Another aspect of the present invention is the provision of compounds useful in apitherapy which greatly reduce the discomfort normally associated with apitherapy. Frequently, apitherapy involves multiple injections of relatively small doses of bee venom at various sites. By way of example only, 1 mL containing 1 mg of bee venom could be administered in as many as 50 injections at the inflicted area and surrounding same. About 0.1 mL doses, each containing 0.1 mg of bee venom, would therefore be delivered via each injection. Each of the 50 injections can cause the pain, burning, itching and irritation, as well as potentially swelling and inflammation normally associated with a bee sting. These are collectively referred to herein as "irritation." It has been found that conventional topically applied anesthetics, are ineffective in overcoming or reducing these unfortunate side effects. They can lessen the discomfort associated with being stuck by a needle but they do little to mitigate the irritation caused by the injected bee venom.

It is quite unexpected, therefore, to find that anesthetics and in particular, topical or local anesthetics, can be injected along with the bee venom, or shortly before or after, directly into the bee venom's injection site. When applied in this manner, even at doses and concentrations far lower than those normally used for topical and local applications for treatments as painful as bee venom, such as below 2%, it has been found that the irritation associated with the injection of bee venom can be reduced appreciably. Indeed, while anesthetics may be used in amounts of 1 to 2% topically, much more is often required for very painful procedures. It was very surprising to learn that amounts as low as 2 mg/injection and less produced meaningful reductions in discomfort. Indeed, it was particularly surprising to observe these advantages at only 10 times the amount of venom administered and below.

Not only was the amount of anesthetic used when applied in this fashion surprising, so too was the way in which it acted. Anesthetics applied topically and intradermally would be expected, at these concentrations and quantities, to provide some form of pain relief for only a few moments. They might help with the initial pain of the injection. However, bee venom can be very painful for as much as 10-15 minutes after injection, much longer than such a small amount of anesthetic should be expected to provide any relief. Yet, it was surprisingly found that anesthetics applied as described herein can actually provide adequate pain relief long after the injection. Indeed, pain relief was consistent. That is to say that patients did not, after 5 or 10 minutes, suddenly realize a higher level of pain as the anesthetic wore off.

Therefore, compounds in accordance with this aspect of the present invention include a therapeutically effective amount of bee venom and at least one anesthetic provided in an amount which is sufficient to reduce the irritation associated with the injection of the bee venom. In one preferred aspect of the present invention, the bee venom and the anesthetic are intermixed and administered as a single preparation. However, the compound in accordance with the present invention may also be produced in situ, in the injection site, by first injecting a patient with the appropriate amount of anesthetic and then the appropriate amount of bee venom or vice versa.

Generally, the anesthetic is provided in a ratio of between about 20:1 to about 1:10 by weight relative to the weight of the bee venom. Preferably, the ratio is 10:1-1:10 by weight. However, more preferably, the anesthetic and bee venom are provided in a 3:1 to about a 1:1 weight ratio. Both the bee venom and the anesthetic are preferably provided in combination with at least one excipient or at least one liquid carrier. The amount of bee venom generally present in each mL of the compounds of this aspect of the present invention range from between about 0.1 to about 10 mg and the bee venom used is preferably the standardized bee venom preparation described above.

The present invention also relates to methods of administering bee venom to a patient so as to reduce the patient's discomfort during treatment by administering, simultaneously or consecutively, as previously discussed, both a therapeutically effective amount of bee venom and at least one anesthetic. Both are administered intradermally, subcutaneously or intramuscularly and to the same injection sites (i.e., if the anesthetic is administered intradermally to a specific spot on a patient's left knee, the bee venom is also administered intradermally to that same spot).

The amount of anesthetic provided in accordance with these methods is an amount which is sufficient to reduce the irritation associated with the injection of the therapeutically effective amount of bee venom. Typically, each injection in accordance with these methods will deliver between about 0.01 to about 1.0 mg of bee venom and more preferably between about 0.05 to about 0.5 mg per injection. Most preferably, about 0.1 mg would be administered per injection. The total amount of bee venom administered per treatment session will depend upon the number of injections. Similarly, the amount of anesthetic administered per injection will range from between about 0.01 to about 10 mg and more preferably between about 0.10 to about 1.0 mg per injection. Most preferably, the amount of anesthetic administered will be about 0.1 mg to about 0.3 mg per injection.

In another aspect of the present invention, there are provided methods of treating rheumatoid, osteo, gouty, psoriatic arthritis, ankylosing spondylitis, fibromyalgia, fibromyositis, myofascial dysfunction pain syndrome, tennis elbow, golfer's elbow, frozen shoulder, bursitis, tendonitis, chronic surgical inflammation of soft and bony tissue, peripheral neuritis, neuralgia, migraine, eczema, psoriasis, multiple sclerosis and lupus as well as other autoimmune, neurological, dermatological and degenerative diseases by the administration of bee venom preparation in the pharmaceutical compounds as described above.

DETAILED DESCRIPTION OF THE PREFERRED EMBODIMENTS

Bee venom, in accordance with the present invention, generally refers to the venom of *Apis mellifera* (the honeybee). The general composition of bee venom is provided in Table 1 below.

TABLE 1

Typical biochemical compositions of the bee venom

| DESCRIPTION | COMPONENT | MOL. WT. | % (DRY VENOM) |
|---|---|---|---|
| Peptides | Melittin | 2,840 | 40-50 |
| | Apamin | 2,036 | 2-3 |
| | MCD-Peptide (Peptide 401) | 2,588 | 2-3 |
| | Adolapin | 11,500 | 1.0 |
| | Protease Inhibitor | 9,000 | <0.8 |
| | Secarpin | | 0.5 |
| | Tertiapin | | 0.1 |
| | Melittin F | | 0.01 |
| | Procamine A, B | | 1.4 |
| | Minimine | 6,000 | 2-3 |
| | Cardiopep? | | <0.7 |
| Enzymes | Hyaluronidase | 38,000 | 1.5-2.0 |
| | Phospholiase A2 | 19,000 | 10-12 |
| | α-Glucosidase | 170,000 | 0.6 |
| | Acid Phosphomponesterase | 55,000 | 1.0 |
| | Lysophospholipase | 22,000 | 1.0 |
| Physiologically Active amines | Histamine | | 0.6-1.6 |
| | Dopamine | | 0.13-1.0 |
| | Norepinephrine | | 0.1-0.7 |
| Nonpeptide Components | Carbohydrates: Glucose and Fructose | | <2.0 |
| | Lipids: 6 Phospholipids | | 4-5 |
| | Amino Acids: γ-Aminobutyric Acid | | <0.5 |
| | β-Aminoisobutyric Acid | | <0.01 |

By weight of the dry venom, the most significant component is a peptide known as melittin which is known to stimulate the hypophyseal-adrenal system and produces cortisone.

It is 100 times more potent than hydrocortisone. Melittin is also known to stabilize lysosome cell membranes which provide protection against inflammation. The other main pharmacological components include apamin, MCD-peptide (also known as peptide 401), adolapin and various protease inhibitors. Apamin works like melittin. It also inhibits the complement system, $C_3$, which is involved in inflammation. MCD-peptide blocks arachidonic acid and inhibits prostaglandin synthesis. Adolapin inhibits microsomal cyclooxygenase. It also inhibits lipoxygenase and thromboxane. Protease inhibitors inhibit carrageenin, prostaglandin $E_1$, bradykinin and histamine induced inflammation, amongst other effects. Therefore, the term "bee venom" as used herein also refers to the administration of one or more of the pharmacologically active components of bee venom, such as melittin or a combination of melittin and peptide 401. The term "bee venom" also, of course, refers to whole venom, as well as to, in the appropriate context, venom or components thereof prepared and purified in accordance with the present invention.

Unlike conventional forms of apitherapy which utilized bee stings, the standardized bee venom preparations preferred in accordance with the present invention are mixed with a liquid carrier. Any carrier which can solublize dried pure bee venom and which is pharmaceutically acceptable for intradermal, subdermal or intramuscular administration may be used in accordance with the present invention. Most preferably, such carriers include sterile and/or deionized water and physiological saline solution, i.e., those containing about 0.9% sodium chloride. Generally, the amount of liquid carrier useful in accordance with the present invention is sufficient to provide a concentration of between about 0.1 to about 10 mg of bee venom per mL. More preferably, the amount of liquid carrier is sufficient to provide a concentration of between about 0.5 and about 5 mg of bee venom per mL. Most preferably, the mixture of liquid carrier and bee venom results about 1 mg of bee venom per mL. For example, 1 g of dried bee venom can be diluted in 1 L (1,000 mL) of normal, injectable, physiological saline (0.9% NaCl). Preferably, this is done at about 20° C. inside a sterile room. The result is a solution containing 1 mg of bee venom per mL. Preferably, the bee venom in accordance with the present invention is whole bee venom.

After filtering through a 25 mcm filter, the standardized bee venom preparation preferably includes between about 0.01 to about 1.0 mg of melittin and about 80 to about 9,500 mcg total protein per mL. More preferably, the resulting pharmaceutical compound includes between about 0.01 to about 0.10 mg of melittin and about 400 to about 4,500 mcg total protein and most preferably, between about 0.04 to about 0.05 mg of melittin and about 800 to 950 mcg of total protein per mL. Most preferably, the bee venom in question will exhibit 40 to 100 HHU/mL of Hyaluronidase activity (diluted to 100 mcg/mL) and is capable of inhibiting gelatin induced aggregation of erythrocytes of 3-5 mm/H.

It will be appreciated that any purification means may be utilized to provide bee venom of similar purity as that resulting from a 25 mcm filter. Such methodologies include normal and reverse phase chromatography, affinity chromatography, recrystallization, immunochemical precipitation, membrane permeation methods as well as other filtration methods.

In addition to the liquid carrier, the bee venom preparations in accordance with the present invention may include other conventional excipients including viscosity modifiers, preservatives and additives such as sodium chloride, various saccharides and the like. These excipients include, without limitation, benzyl alcohol and methylparaban, Ringers solution and other physiologically acceptable materials commonly used in injectable therapeutics.

Typical formulations in accordance with this aspect of the present invention include 1.0 mg of pure dried *Apis mellifera* venom and 9.0 mg of sodium chloride per each mL of water. Another preferred formulation comprises 1.0 mg of pure dried *Apis mellifera* venom, 9.0 mg of sodium chloride and 0.009 mL of benzyl alcohol plus 0.991 mL of water. Again, these formulations are preferably filtered through a filtering device which will exclude anything over at least 25 mcm. The use of even finer grade filtering is also contemplated.

When used alone for the treatment of various conditions such as arthritis or multiple sclerosis, or the relief of joint or back pain, for example, multiple doses are typically administered. Generally, bee venom is administered over a course of six to twelve weeks in one or more sessions per week and a number of injections can increase from one or two injections to twenty to fifty or more injections per session. The amount of bee venom, as described herein, which may be administered with each injection may range from between about 0.01 to about 1 mg. Preferably, the amount of bee venom administered is between about 0.05 and about 0.5 mg per injection, and more preferably about 0.1 mg per injection. Thus, 1 mL of either of the two formulations described immediately above can be provided in 10 divided doses of 0.1 mL each with each dose delivering 0.1 mg of bee venom.

Generally in accordance with the present invention, the bee venom containing solution is administered intradermally using a suitable sterile syringe with 0.1 mL graduations and a 25 or 27 gauge needle. The needle should generally range from between about ¼" to about ⅝" long. It is appropriate to undertake skin testing of the patient before the first treatment to determine possibility of allergic reaction. A suitable testing area such as the flexor surface of the forearm is used at about ½ of the normal dose, or 0.05 mL, slowly injected to make a small hemispherical bleb. The interpretation of the skin response is based on the size of wheal, size of erythema and the appearance of irregular spreading, pseudo-pod projections from the test area. A normal response appears when there is a pinpoint blood spot which indicates needle insertion, a wheal having a diameter of 0.5 to about 1.0 cm and erythematous changes from about 1" to about 2" surrounding the injection site. If no systemic reactions occur within 15 to 30 minutes after injection, the test is considered negative.

When administering intradermally, prior to injection, it is often advisable to withdraw the plunger and observe for blood entering the syringe to avoid intravascular injection. The injections are given in different places dependent upon the affliction. However, for the purposes of mitigating pain and treating arthritis, for example, the injections are given in the painful area first. Most preferably, the injections are given to the tender point or trigger points. Later, one may give injections to the spinal area according to the dermatome chart for maximum effect. Generally, during the course of treatment, alcohol consumption is forbidden, ice packs or mentholated ointment may be applied if local reactions occur and if generalized itching occurs, Benadryl may be taken, preferably in the amount of about 75 mg at bedtime and about 50 mg during the day. Acetaminophen or other antipyretics may be taken as indicated for low grade fever or chills.

This invention also contemplates an apparatus for the collection of venom from honeybees in the purest way using a low voltage electric shock method. The extractor consists of two wooden frames one inside the other. The electric wires are attached to the front surface of the outer frame and the wires are alternately grounded and charged. When a bee comes into contact with two consecutive wires it completes the circuit between the wires and as a result is shocked.

The extractor is placed in front of the hive and connected with an electric timer to a nine volt battery. When the battery is connected, current is allowed to flow alternatively, five seconds on and three seconds off. As soon as the device is turned on, the bees in the hives get excited and start to come out to attack the extractor. At the same time, they spread pheromones into the air which makes other bees angry. When the bees get the electric shock, they bend their lower abdomen and force their stingers into a silicone rubber sheet stretched across one portion of the inner frame. When electricity is off for three seconds, they withdraw their stinger so that they do not die. Pure liquid bee venom is deposited on the underside of the silicone rubber sheet. The inner frame is removed from the outer frame and placed in a sterile box.

The box can be placed in the sterile refrigerator (4° C.) for four to six hours to allow it to air dry. The inner frame will then be taken out of the box and placed in a large sterile cage. Dried venom crystals are easily scraped off using a medical blade. The collected crystallized venom is then put in a sterilized bottle and it is sealed. The venom may also be collected as described in U.S. Pat. Nos. 4,739,531 and 3,163,871, the text of which is hereby incorporated by reference.

The use of the standardized formulations in accordance with the present invention in the treatment of various conditions, particularly those described herein, represents a significant advancement over the art. However, being stung by a bee is not a pleasant experience. Being stung 30 times or more certainly raises the level of discomfort. The painful burning sensation experienced by the use of bee venom is unlike other forms of pain and irritation. And while standardized formulations administered intradermally, as preferred in accordance with the present invention, is far more palatable than actual bee stings, the irritation associated with the administration of bee venom can still represent a deterrent to the use of apitherapy. Therefore, in a preferred aspect of the present invention there is provided compositions and methods which mitigate, reduce and, in some instances, even eliminate the irritation associated with the injection of bee venom. This discovery is surprising. First, the use of anesthetics and, in particular, topically applied local anesthetics, does not provide relief from the burning, stinging and other forms of irritation which generally result from, for example, intradermal introduction of bee venom. Yet the concurrent or simultaneous administration of an anesthetic to the same injection site does result in relief.

Unfortunately, the introduction of an anesthetic in this way was found to generate problems not otherwise anticipated. For example, when an appropriate amount of a 2% solution of lidocaine was used, (20 mg/mL lidocaine:1 mg/ml bee venom) significant relief from the stinging, burning and other forms of irritation associated with the intradermal administration of bee venom was realized. However, the lidocaine itself caused irritation which was not associated with the bee venom. The result was a significant improvement over the use of bee venom alone. However, the fact that lidocaine used in amounts which were typically appropriate for, for example, topical or local use, could be associated with additional irritation when used in combination with bee venom was surprising.

It was also unexpectedly found that one could reduce the relative amount of anesthetic introduced to levels far below those generally used in topical and local applications (i.e., 1% and below) resulting in both a significant reduction in the irritation associated with the injection of the bee venom and, at the same time, the elimination of the irritation associated with, for example, intradermal administration of the anesthetic.

In accordance with this aspect of the present invention, the bee venom used may be that described previously or any other bee venom preparation, purified, filtered or not. The pharmaceutical compounds in question may include the anesthetic mixed into a single solution and administrated in a single syringe. It is not necessary, however, that the bee venom and the anesthetic be injected in a single formulation or even simultaneously. The anesthetic can be formulated separately and administered to the same injection site either after or, more preferably, immediately before the injection of the bee venom. When consecutively administered, it is preferable that the anesthetic be injected no more than an hour before and no longer than 10 minutes after the introduction of the bee venom. More preferably, when consecutively administering the bee venom and anesthetic, the anesthetic is administered within 10 minutes of the bee venom, preferably, within just a few moments before or after. Most preferably, the anesthetic is administered immediately before or immediately after the bee venom.

If the bee venom is to be administered intramuscularly, then the anesthetic should also be administered to the same injection site intramuscularly. The same thing holds true for subdermal or subcutaneous and, most preferably, intradermal administration.

The degree to which irritation associated with the injection of the bee venom is reduced is somewhat subjective. It would depend on a number of factors such as, for example, the individual patient's threshold for pain, the number of injections and the amount of bee venom administered with each injection, the location of the injection site and the depth of injection, intradermal, subcutaneous or intramuscular. However, generally speaking, by the use of an appropriate amount of anesthetic as described and claimed herein, the degree of irritation will be reduced relative to the administration of the same dose, in the same protocol to the same patient without the anesthetic.

Anesthetics in accordance with the present invention include any compound which can reduce the irritation associated with the injection of bee venom. Anesthetics need not be topical or local anesthetics. However, such anesthetics are preferred. In particular, anesthetics useful in accordance with the present invention include: Ambucaine, Amolanone, Amylocaine Hydrochloride, Benoxinate, Benzocaine, Betoxycaine, Biphenamine, Bupivacaine, Butacaine, Butamben, Butanilicaine, Butethamine, Butoxycaine, Carticaine, Chloroprocaine Hydrochloride, Cocaethylene, Cocaine, Cyclomethycaine, Dibucaine Hydrochloride, Dimethisoquin, Dimethocaine, Diperodon Hydrochloride, Dyclonine, Ecgonidine, Ecgonine, Ethyl Chloride, Etidocaine, β-Eucaine, Euprocin, Fenalcomine, Fomocaine, Hexylcaine Hydrochloride, Hydroxytetracaine, Isobutyl p-Aminobenzoate, Leucinocaine Mesylate, Levoxadrol, Lidocaine, Mepivacaine, Meprylcaine, Metabutoxycaine, Methyl Chloride, Myrtecaine, Naepaine, Octacaine, Orthocaine, Oxethazaine, Parethoxycaine, Phenacaine Hydrochloride, Phenol, Piperocaine, Piridocaine, Polidocanol, Plidocanol, Pramoxine, Prilocaine, Procaine, Propanocaine, Proparacaine, Propipocaine, Propoxycaine Hydrochloride, Pseudococaine, Pyrrocaine, Ropivacaine, Salicyl Alcohol, Tetracaine Hydrochloride, Tolycaine, Trimecaine, and Zolamine. The most preferred of these, in accordance with the present invention, is lidocaine.

Understandably, the amount of anesthetic used is generally controlled by the amount of bee venom used. However, the amount may need to be adjusted based on the specifics of the patient's condition, sensitivity to pain or the exact course of treatment. Generally, the amount of anesthetic is provided in a ratio of between about 20:1 to about 1:10 by weight relative to the weight of the bee venom. More preferably, the anesthetic is provided in a ratio of about 10:1 to about 1:5 by weight and more preferably between about 3:1 to about 1:1 by weight.

The liquid carriers and/or excipients used to formulate the anesthetic in accordance with the present invention may be the same or different as that used in formulating the bee venom. It is also possible that the anesthetic is a liquid or is purchased in a formulation in which it is premixed with one or more carriers and/or excipients. In that case, no additional carriers or excipients need be used for the anesthetic. Furthermore, these types of anesthetic formulations could themselves be used as the carrier for the bee venom or mixed with a liquid bee venom formulation such as that described above.

The amount of anesthetic administered is preferably between about 0.01 and about 2.0 mg per injection and more preferably between about 0.05 and about 1.0 mg per injection. Most preferably, the amount of anesthetic administered in each injection is about 0.1 mg per injection.

Typical formulations include: (1) each mL contains pure dried *Apis mellifera* venom 1.0 mg, sodium chloride 9.0 mg, and lidocaine hydrochloride 1.0 mg in 1 mL water for injection; (2) each mL contains pure dried *Apis mellifera* venom 1.0 mg, sodium chloride 9.0 mg, lidocaine hydrochloride 1.0 mg, and benzyl alcohol 0.009 mL in 0.991 mL of water for injection; and (3) each mL contains pure dried *Apis mellifera* venom 1.0 mg, sodium chloride 9.0 mg, lidocaine hydrochloride 1.0 mg and methylparaban 0.1 mg in 1 mL of water for injection.

EXAMPLES

All of the patients in the following examples had been previously treated with standard medical therapies and yet significant pain persisted. Multiple medications including analgesics, muscle relaxants, non-steroidal anti-inflammatories, various injections, chiropractic manipulation, physical therapy, and even surgery often failed to relieve patients medical conditions and in particular, their pain.

The examples were performed using a bee venom/lidocaine dosage form of 0.1 mL per injection of a solution of 1:1 bee venom to lidocaine for each dose given from the sixth session on. Prior sessions used bee venom alone. The solutions were formulated with normal saline (9.0 mg/mL) and was filtered through a 25 mcm filter. Each patient was injected with individual injections of 0.1 mL per injection. The number of injections varied with the condition and number of treatments.

In each of the examples, the patients were treated by intradermal injections with formulations in accordance with the present invention twice a week on average for 12 to 20 sessions. In the following examples, "RA Titer" is a blood test commonly used in diagnosis of Rheumatoid Arthritis. A titer score of less than 20 is considered negative which is, in this case, a desirable result. "ESR" stands for "erythrocyte sedimentation rate" which is used as an indicator of an inflammatory condition. Normal is considered on a scale of 1 to 10. Anything higher is problematic and indicates generalized inflammation.

"ROM" means range of motion. The standard for range of motion changes depending on the joint in question. However, the greater the distance between the two end points, the greater the range of motion. Tenderness and swelling are graded on a standard scale using plus signs. Each plus sign generally indicates approximately 20%. The maximum number of plusses (5) indicate a maximum amount of tenderness and/or swelling. "VAS" stands for visual analog scale. This is a method widely recognized for pain measurement. The most common VAS consists of 100 mm horizontal line with two end points labeled no pain and worst pain ever. The patient is requested to place a mark on the 100 mm line at the point which corresponds to the level of pain intensity he or she presently feels. The distance in millimeters from the low end of the VAS to the patient's mark is used as the numerical index of severity of pain. This procedure has been published in Churchill Livingston, Textbook of Pain, New York, 3d ed. 1994 338-339 and in Lea and Febiger, The Management of Pain, Philadelphia, 2d ed. 1990 581-582.

Example 1

Rheumatoid Arthritis (RA)

NG is a 39 year old female who suffered from RA for 19 years. She tried every possible treatment including a cancer therapy drug to help her condition. The pain and swelling in her hands and wrists were unbearable and she became disabled. She had 24 sessions of therapy in accordance with the present invention with 95% improvement. Her condition stabilized and no more pain and swelling was noted.

|  | Before Treatment | After Treatment |
| --- | --- | --- |
| RA Titer (<20 = Negative) | 268 | 18 |
| ESR (Normal: 0-10) | 49 | 7 |
| ROM (Flextion: 0-70) | Wrist - Rt: 15, Lt: 10 | Wrist - Rt: 55, Lt: 60 |
| Tenderness & Swelling | +++++ | + |
| VAS (Pain Index) | 98 | 15 |

Example 2

Osteoarthritis

HR is a 75 year old female who suffered from degenerative arthritis for over 25 years. Her knees and spine were more involved than other joints. She had 18 treatments in accordance with the present invention and her condition markedly improved. She stopped taking all the medications and is doing well.

|  | Before Treatment | After Treatment |
| --- | --- | --- |
| Tenderness & Swelling | +++ | 0 |
| ROM (Fl-Ext: 0-120) | Knees - Rt: 60, Lt: 75 | Knees - Rt: 100, Lt: 110 |
| VAS (Pain Level) | 73 | 16 |

Example 3

Ankylosing Spondylitis

MO is a 53 year old female who had long-standing low back problems and multiple operations with fusions. She had 18 months rehabilitation therapy without relief. She had a total of 26 treatments in accordance with the present invention with moderate improvement. No more medications were needed. Follow-up visits monthly when it is necessary.

|  | Before Treatment | After Treatment |
|---|---|---|
| Tenderness & Swelling | +++++ | + |
| VAS (Pain Level) | 95 | 20 |

Example 4

Fibromyalgia

PA is a 32 year old female who suffered with Fibromyalgia. All prior medical and psychological treatments were unsuccessful. Trigger point injections were given in multiple areas. Total 16 treatments with complete relief. Note—a "trigger point" is an area which, when stimulated, causes a sudden pain in a specific area.

|  | Before Treatment | After Treatment |
|---|---|---|
| Multiple Trigger Points | 14 | 0 |
| VAS (Pain Level) | 82 | 17 |

Example 5

Tennis Elbow

JK is a 43 year old male who suffered from "Tennis Elbow" for 4 years. Conventional approaches failed. After a total of 12 treatment sessions with formulations in accordance with the present invention, his recovery was nearly complete.

|  | Before Treatment | After Treatment |
|---|---|---|
| Tenderness & Swelling | +++++ | + |
| VAS (Pain Level) | 65 | 0 |

Example 6

Frozen Shoulder (Adhesive Capsulitis)

BO is a 56 year old male with Frozen Shoulder. Medications, injections and an operation failed. His range of motion was limited to 20% with constant pain. After 14 treatment sessions with formulations in accordance with the present invention, his recovery was complete.

|  | Before Treatment | After Treatment |
|---|---|---|
| Tenderness | ++++ | 0 |
| ROM | Limited to 20% | Full Motion |
| VAS (Pain Level) | 85 | 5 |

Example 7

Chronic Surgical Inflammation

BC is a 49 year old male who had more than 10 abdominal surgeries due to bleeding ulcers, alcoholic chirrosis and intestinal obstructions. Due to a phantom gallbladder pain and surgical pain, he was heavily addicted to medications. After 28 treatment sessions with formulations in accordance with the present invention, and with the injections concentrating at surgical scars, relief was nearly 100%.

|  | Before Treatment | After Treatment |
|---|---|---|
| Tenderness | +++++ | + |
| VAS (Pain Level) | 92 | 14 |

Example 8

Postherpetic Neuralgia (PHN)

JP is a 78 year old female who suffered from shingles. Medical and surgical treatments failed. She experienced a nearly 90% improvement after 16 treatments in accordance with the present invention. Note—a "bleb" is a blister or bulla.

|  | Before Treatment | After Treatment |
|---|---|---|
| Blebs at Thoracic Area | +++ | 0 |
| Hypersensitivity (Touch) | +++++ | + |
| VAS (Pain Level) | 100 | 28 |

Example 9

Psoriasis

TH is a 28 year old male who suffered from psoriasis for 7 years. Medications were helping only temporarily. His condition was severe, so that he could not wear short pants even on hot summer days. After a total of 24 sessions, marked improvement was realized. Follow-up treatment was required at least once a month.

Example 10

Multiple Sclerosis (MS)

SR is a 47 year old female with multiple sclerosis for 15 years. Despite all the conventional treatments, her condition progressively worsened. She continuously felt tingling and numbness in her legs, lost 40% of bladder control, lost strength in her extremities and her balance was so terrible that she had to depend upon a cane or walker. After a total of 28 treatment sessions, a marked improvement was observed in her condition. Her bladder control is now 100% and she no longer needs a cane or walker. She requires follow-up visits every 3 to 4 weeks for foreseeable future.

|                      | Before Treatment | After Treatment |
|----------------------|------------------|-----------------|
| Muscle Weakness      | ++++             | +               |
| Spasticity           | +++++            | ++              |
| Bladder Control      | 60%              | 100%            |
| Balance              | Poor             | Good            |
| Using a Cane or Walker | Yes            | No              |

Example 11

Pain

Thirty patients, including the 10 patients described in Examples 1-10 were treated with the appropriate amount of bee venom alone for the first five (5) sessions. All subsequent sessions (number varied from patient to patient) were treated with a solution of 1:1 bee venom to lidocaine as described under the general heading "Examples" above. Patients were never told which formulation they were given and patients were asked about the level and type of pain and discomfort realized after each treatment. Patients were also checked for body language, degree of wincing, reluctance to treatment, etc.

97% of patients objectively reported lower injection site pain and discomfort using the venom/lidocaine formulation. There was less fear about further injections, and since using this invention, the number of patients who drop out of treatment has dropped dramatically. The pain relief was consistent in that patients did not experience a sudden increase in pain as would be expected from the relatively short lived pain relief otherwise expected for small doses of these types of anesthetics.

The invention claimed is:

1. A standardized bee venom preparation comprising a liquid carrier, from about 0.1 milligram (mg) to about 1.0 mg of pure melittin, and from about 400 microgram (mcg) to about 4,500 mcg of total protein per milliliter (mL) of said standardized bee venom preparation, wherein said standardized bee venom preparation exhibits 40 to 100 honey bee hyaluronidase units per mL (HHU/mL) of hyaluronidase activity when diluted to 100 mcg/mL and is capable of inhibiting gelatin induced aggregation of erythrocytes of 3-5 millimeter per hour (mm/H).

2. The standardized bee venom preparation of claim 1, wherein the liquid carrier is sterile deionized water or physiological saline solution.

3. The standardized bee venom preparation of claim 1, further comprising an excipient selected from the group consisting of a viscosity modifier, preservative, additive, sodium chloride, saccharide, benzyl alcohol, methyl paraban and mixtures thereof.

4. The standardized bee venom preparation of claim 1, further comprising an anesthetic.

5. The standardized bee venom preparation of claim 4, wherein said anesthetic is selected from the group consisting of ambucaine, amolanone, amylocaine hydrochloride, benoxinate, benzocaine, betoxycaine, biphenamine, bupivacaine, butacaine, butamben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperodon hydrochloride, dyclonine, ecgonidine, ecgonine, ethyl chloride, etidocaine, β eucaine, euprocin, fenalcomine, fomocaine, hexylcaine hydrochloride, hydroxytetracaine, isobutyl p aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, plidocanol, pramoxine, prilocaine, procaine, propanocaine, proparacaine, propipocaine, propoxycaine hydrochloride, pseudococaine, pyrrocaine, ropivacaine, salicyl alcohol, tetracaine hydrochloride, tolycaine, trimecaine, zolamine, and mixtures thereof.

6. The standardized bee venom preparation of claim 4, wherein said anesthetic is lidocaine.

7. The standardized bee venom preparation of claim 4, wherein the amount of said anesthetic provided is in a ratio of between about 20:1 to about 1:10 by weight relative to the weight of said standardized bee venom preparation.

8. The standardized bee venom preparation of claim 7, wherein the amount of said anesthetic provided is in a ratio of between 10:1 to about 1:5 by weight relative to the weight of said standardized bee venom preparation.

9. The standardized bee venom preparation of claim 8, wherein the amount of said anesthetic provided is in a ratio of between 3:1 to about 1:1 by weight relative to the weight of said standardized bee venom preparation.

10. A method of treating rheumatoid, osteoarthritis, gouty arthritis, psoriatic arthritis, psoriasis, ankylosing spondylitis, fibromyalgia, fibromyositis, myofascial dysfunction pain syndrome, tennis elbow, golfer's elbow, frozen shoulder, bursitis, tendonitis, chronic surgical inflammation of soft and bony tissue, peripheral neuritis, neuralgia, migraine, eczema, multiple sclerosis or lupus comprising administering the standardized bee venom preparation of claim 1 to a patient in need thereof.

11. The method of claim 10, wherein the standardized bee venom preparation of claim 1 is administered to the patient via the intradermal, intramuscular, subdermal or subcutaneous route.

* * * * *